(12) United States Patent
Ratzmann

(10) Patent No.: US 7,769,128 B2
(45) Date of Patent: *Aug. 3, 2010

(54) SUPPORT STRUCTURE FOR Z-EXTENSIBLE CT DETECTORS AND METHODS OF MAKING SAME

(75) Inventor: Paul M. Ratzmann, Germantown, WI (US)

(73) Assignee: General Electric Company, Schenectady, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 11/619,112

(22) Filed: Jan. 2, 2007

(65) Prior Publication Data

US 2007/0104312 A1    May 10, 2007

Related U.S. Application Data

(63) Continuation of application No. 10/324,235, filed on Dec. 19, 2002, now Pat. No. 7,190,759.

(51) Int. Cl.
     *A61B 6/03*       (2006.01)
     *H05G 1/64*       (2006.01)

(52) U.S. Cl. .................... 378/19; 378/98.8; 250/370.09

(58) Field of Classification Search ............ 378/19, 378/98.8; 250/370.09
See application file for complete search history.

(56) References Cited

U.S. PATENT DOCUMENTS

| | | | |
|---|---|---|---|
| 4,181,856 A * | 1/1980 | Bone ................ 250/370.09 |
| 5,487,098 A | 1/1996 | Dobbs et al. |
| 5,635,718 A | 6/1997 | DePuydt et al. |
| 5,668,851 A | 9/1997 | Dobbs |
| 5,830,273 A * | 11/1998 | Zimmerman ............. 118/502 |
| 5,848,116 A | 12/1998 | Sugihara |
| 5,955,733 A | 9/1999 | Orava et al. |
| 6,144,718 A * | 11/2000 | Hoffman et al. .......... 378/19 |
| 6,396,898 B1 | 5/2002 | Saito et al. |
| 6,424,697 B1 | 7/2002 | Zastrow et al. |
| 6,426,991 B1 | 7/2002 | Mattson et al. |
| 6,510,195 B1 | 1/2003 | Chappo et al. |
| 6,587,538 B2 * | 7/2003 | Igarashi et al. ........... 378/19 |
| 6,717,150 B2 | 4/2004 | Hoffman |

(Continued)

FOREIGN PATENT DOCUMENTS

JP      2001153960 A     6/2001

(Continued)

*Primary Examiner*—Allen C. Ho
(74) *Attorney, Agent, or Firm*—Ziolkowski Patent Solutions Group, SC

(57) ABSTRACT

Pin-based support structures for easily and precisely assembling CT detector components into individual detector modules are described, as are methods of making the same. The pins in these structures serve as the local reference points against which all other detector components (i.e., collimators, scintillator packs, diodes, electronic flex connectors, etc.) are aligned. The pins may also be used to quickly and easily attach the individual detector modules to the local detector reference frame and then to the global reference frame in a CT imaging system. These structures allow CT detector components to be more easily and economically assembled than previously possible. Furthermore, these structures are extensible in the Z-direction, allowing for longer Z-coverage with each rotation of the gantry, thereby allowing for full organ imaging in a single CT scan.

21 Claims, 3 Drawing Sheets

U.S. PATENT DOCUMENTS

| | | | |
|---|---|---|---|
| 6,778,637 B2 * | 8/2004 | Luhta et al. | 378/154 |
| 6,917,664 B2 | 7/2005 | Chappo et al. | |
| 6,982,423 B2 * | 1/2006 | Elgali | 250/370.11 |
| 7,177,387 B2 * | 2/2007 | Yasunaga et al. | 378/19 |
| 7,190,759 B2 * | 3/2007 | Ratzmann | 378/19 |
| 7,259,376 B2 * | 8/2007 | Pohan | 250/370.09 |
| 7,492,857 B2 * | 2/2009 | Yasunaga et al. | 378/19 |
| 7,564,940 B2 * | 7/2009 | Mattson et al. | 378/19 |
| 2002/0064252 A1 | 5/2002 | Igarashi et al. | |
| 2004/0065465 A1 | 4/2004 | Chappo et al. | |
| 2004/0065839 A1 | 4/2004 | Elgali | |

FOREIGN PATENT DOCUMENTS

| | | |
|---|---|---|
| JP | 2002202376 A | 7/2002 |

* cited by examiner

SUPPORT STRUCTURE FOR Z-EXTENSIBLE CT DETECTORS AND METHODS OF MAKING SAME

The present application is a continuation and claims priority of U.S. patent application Ser. No. 10/324,235 filed Dec. 19, 2002, now U.S. Pat. No. 7,190,759 B2, the disclosure of which is incorporated herein.

FIELD OF THE INVENTION

The present invention relates generally to a support structure and assembly method for Z-extensible computed tomography (CT) detectors. More specifically, the present invention relates to a pin-based support structure module, wherein the pins provide the reference points upon which all other components of a CT detector are aligned so as to allow for easy and precise placement of all components thereof, and methods of making same.

BACKGROUND OF THE INVENTION

CT imaging systems utilize a fan-shaped x-ray beam that is collimated to lie within the X-Y plane, or the imaging plane. The x-ray beam is attenuated by the object being imaged (i.e., the patient having the CT scan performed on them), and the x-ray is then detected by an array of radiation detectors. Generally, this array of radiation detectors comprises a plurality of individual detector modules, with each detector module forming a flat detector surface. The detector modules are generally positioned together in a side-by-side manner to form an arc that is essentially centered on the x-ray source. In multi-slice imaging systems, parallel rows of these detector modules may be arranged so that data corresponding to each single array row can be used to generate a single thin slice image through a patient.

Behind the flat detector surface, each detector module comprises rows and columns of detector elements aligned with X and Z coordinates, respectively. Additionally, each detector module generally comprises data acquisition circuitry that collects the x-ray intensity signals that are generated by the detector elements, and then converts these intensity signals into CT numbers (i.e., Hounsfield units) which are stored for subsequent image reconstruction via back projection or the like. Various other components, such as post-patient collimators, scintillator packs, photo diodes, and electronic flex connectors, may also be attached to these detector modules. All such attachments must be precisely located with respect to one another, making the manufacture of current CT imaging systems very difficult. As such, extensive testing, reworking and realignment of the various components is often required before a CT imaging system of acceptable quality can be shipped to a customer.

As there are presently no suitable systems and methods that allow CT detector components to be easily and accurately assembled, it would be desirable to have systems and methods in which such components could be more easily assembled than currently possible. There is also a need for such systems and methods to allow such components to be precisely and accurately assembled. There is also a need for such systems and methods to utilize pins as reference points upon which all other detector components can be aligned. There is still a further need for such systems and methods to allow all the detector components to be assembled into a single assembly module, which can then be easily positioned and aligned in the CT imaging system. There is yet a further need for such systems and methods to be less expensive than current assembly systems and methods. Many other needs will also be met by this invention, as will become more apparent throughout the remainder of the disclosure that follows.

SUMMARY OF THE INVENTION

Accordingly, the above-identified shortcomings of existing systems and methods are overcome by embodiments of the present invention, which relates to systems and methods that allow CT detector components to be more easily assembled than currently possible, allowing the detector components to be precisely and accurately assembled into a module, which can then be easily positioned and aligned in a CT imaging system. These systems and methods utilize pins as reference points upon which all the other detector components can be aligned. Many embodiments of this invention are less expensive than the current systems and methods for assembling CT detector components.

Embodiments of this invention comprise precisely-aligned CT detector modules. These detector modules may comprise: a support structure; at least one spacer; at least one alignment pin operatively coupled to the at least one spacer and the support structure to form a support structure sub-assembly; and a detector component operatively coupled to the support structure sub-assembly, wherein the at least one alignment pin is utilized as a local reference point against which the support structure, the at least one spacer, and the detector component are precisely aligned.

Other embodiments of this invention comprise methods for easily and accurately assembling a precisely-aligned CT detector module. These methods may comprise: aligning a support structure, at least one spacer, and at least one alignment pin to one another; operatively coupling the support structure, the at least one spacer, and the at least one alignment pin to one another to form a support structure sub-assembly; aligning a detector component relative to the at least one alignment pin; and operatively coupling the detector component to the support structure sub-assembly, wherein the at least one alignment pin is utilized as a local reference point against which the support structure, the at least one spacer, and the detector component are precisely aligned. An assembly fixture may be utilized to align and assemble the detector module. Embodiments may further comprise operatively coupling a collimator assembly to the detector module and/or operatively coupling the detector module to the reference frame of the detector assembly and the global reference frame of a CT imaging system.

Yet other embodiments of this invention comprise systems for easily and accurately assembling a precisely-aligned detector module. These systems may comprise: a means for aligning a support structure, at least one spacer, and at least one alignment pin to one another; a means for operatively coupling the support structure, the at least one spacer, and the at least one alignment pin to one another to form a support structure sub-assembly; a means for aligning a detector component relative to the at least one alignment pin; and a means for operatively coupling the detector component to the support structure sub-assembly, wherein the at least one alignment pin is utilized as a local reference point against which the support structure, the at least one spacer, and the detector component are precisely aligned. An assembly fixture may be utilized to align and assemble the detector module. Systems may further comprise a means for operatively coupling a collimator assembly to the detector module and/or a means for operatively coupling the detector module to a CT imaging system.

In many embodiments, the detector components may comprise, among other things, an electronic flex connector, at least one diode, and at least one scintillator pack, wherein the electronic flex connector is operatively coupled to the at least one diode and a data acquisition system, and the at least one scintillator pack is operatively coupled to the at least one diode. The detector module may also comprise a collimator assembly operatively coupled thereto. The electronic flex connector, the at least one diode, the at least one scintillator pack, and/or the collimator assembly are preferably all precisely aligned relative to the at least one alignment pin. These detector modules may be operatively coupled to a CT imaging system, which is also preferably precisely aligned relative to the at least one alignment pin. A top surface of the spacer and a bottom surface of the spacer preferably each meet a predetermined flatness requirement, and they also preferably meet a predetermined co-planarity requirement with respect to one another. The at least one alignment pin preferably meets a predetermined diameter requirement, and when the at least one alignment pin is inserted into an aperture in the at least one spacer, the at least one alignment pin preferably meets a predetermined perpendicularity requirement with the top surface of the spacer and the bottom surface of the spacer.

Further features, aspects and advantages of the present invention will be more readily apparent to those skilled in the art during the course of the following description, wherein references are made to the accompanying figures which illustrate some preferred forms of the present invention, and wherein like characters of reference designate like parts throughout the drawings.

DESCRIPTION OF THE DRAWINGS

The systems and methods of the present invention are described herein below with reference to various figures, in which.

DETAILED DESCRIPTION OF THE INVENTION

For the purposes of promoting an understanding of the invention, reference will now be made to some preferred embodiments of the present invention as illustrated in FIGS. 1-4, and specific language used to describe the same. The terminology used herein is for the purpose of description, not limitation. Specific structural and functional details disclosed herein are not to be interpreted as limiting, but merely as a basis for the claims as a representative basis for teaching one skilled in the art to variously employ the present invention. Any modifications or variations in the depicted support structures and methods of making same, and such further applications of the principles of the invention as illustrated herein, as would normally occur to one skilled in the art, are considered to be within the spirit of this invention.

Figure 1:
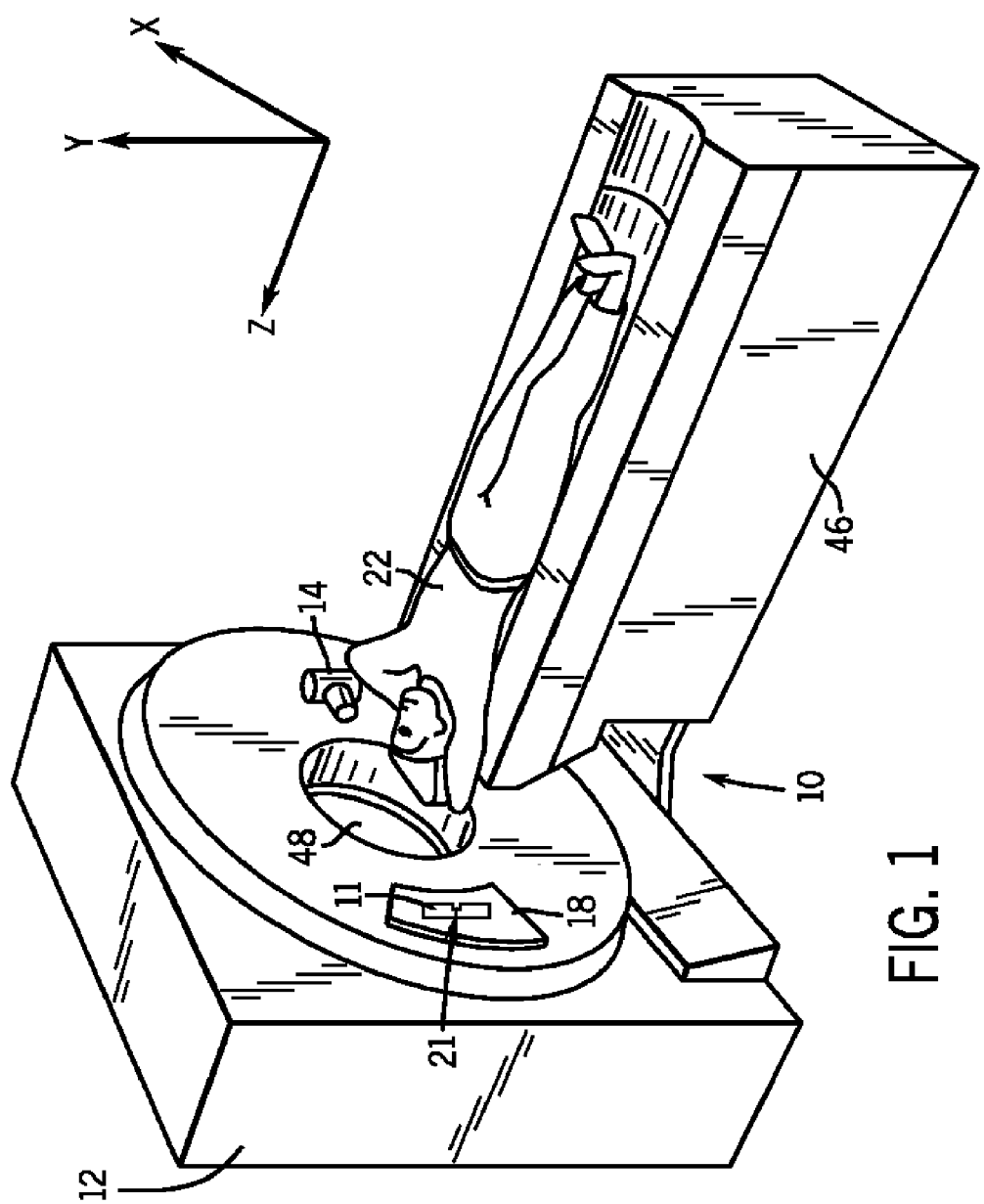
FIG. 1 is perspective view of a CT imaging system.

FIG. 1 shows an exemplary CT imaging system 10. Such systems generally comprise a gantry 12, a gantry opening 48, and a table 46 upon which a patient 22 may lie. Gantry 12 comprises an x-ray source 14 that projects a beam of x-rays 16 toward an array of detector elements 18. Generally, the array of detector elements 18 comprises a plurality of individual detector elements that are arranged in a side-by-side manner in the form of an arc that is essentially centered on x-ray source 14. In multi-slice imaging systems, parallel rows of arrays of detector elements 18 can be arranged so that each row of detectors can be used to generate a single thin slice image through patient 22 in the X-Y plane. Each detector element in the array of detector elements 18 senses and detects the x-rays 16 that pass through an object, such as patient 22.

Each row/array of detector elements 18 in this invention comprises a plurality of detector modules 50, wherein each detector module 50 comprises all the relevant detector components (i.e., diodes, scintillator packs, collimators, etc.) in a single pre-assembled assembly, which may then be easily positioned within CT imaging system 10. The present invention comprises systems and methods that allow these CT radiation detector modules 50 to be very accurately and easily assembled. These detector modules 50 comprise a support structure 52 and spacers 56 that allow all the detector components to be assembled together into a single assembly that can then be easily aligned and inserted into a CT imaging system 10. This invention utilizes pins 55 in the spacers 56 (i.e., the pin/spacer assembly) as the reference points upon which all other detector module components (i.e., diodes, scintillator packs, collimators, etc.) are aligned, thereby allowing for easy and precise placement of all detector components. This pin-based support structure has many advantages: (1) the pins provide parallel surfaces for mounting the detector module components upon; (2) the pins allow the detector module to be precisely positioned and aligned in a CT imaging system; (3) the pins provide optical and mechanical reference features for positioning the diode and scintillator pack(s) during assembly of the detector modules; (4) the pins provide a precise mechanical location where a post-patient collimator may be attached thereto; and (5) the pins allow the detector modules to be mechanically aligned and attached to the final CT imaging system (i.e., via elongated slots 21 in the support rails 11 in some current CT imaging systems).

Figure 2:
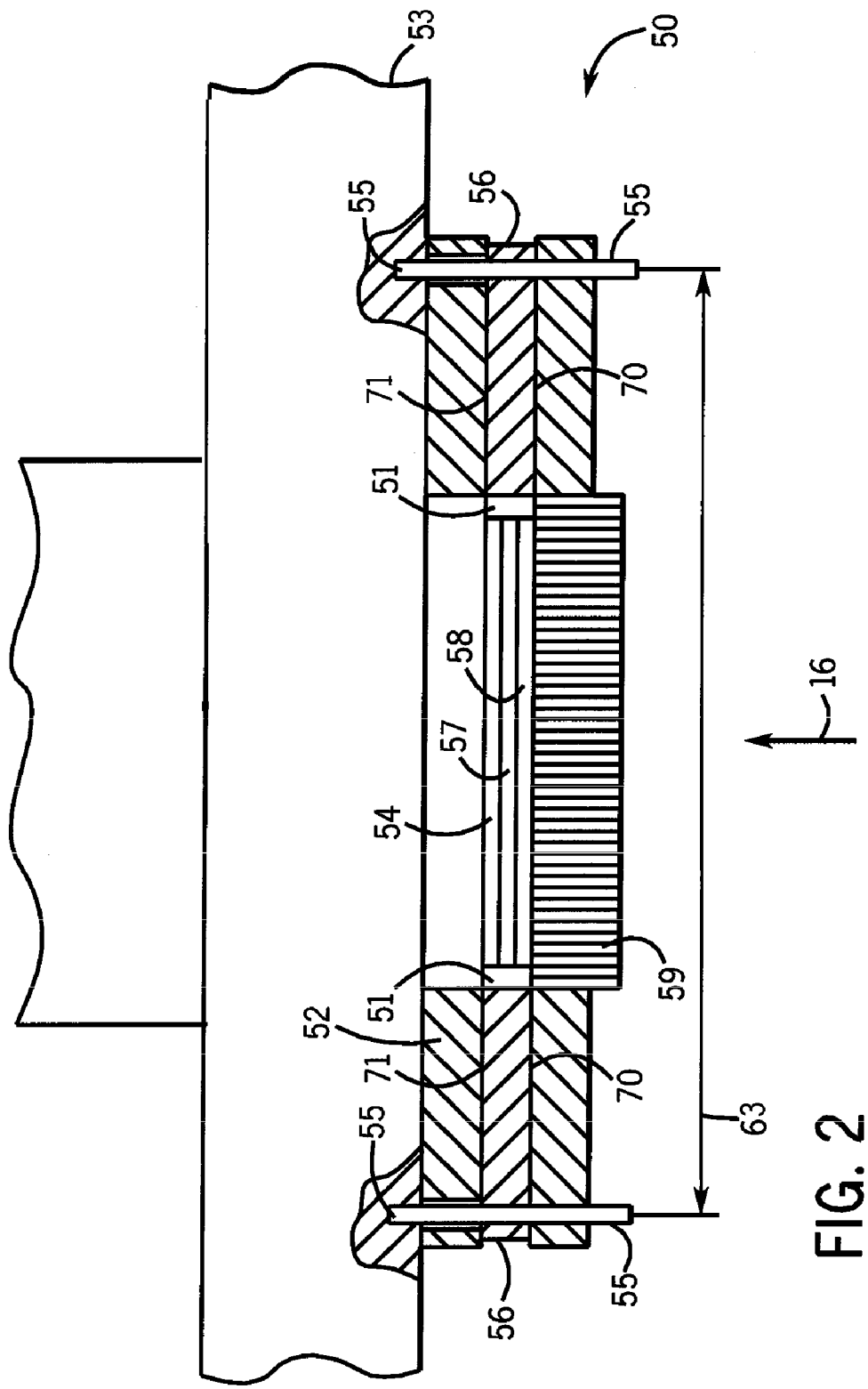
FIG. 2 is a side view showing the basic components of a detector module utilized in embodiments of this invention.

A side view of a detector module 50 as assembled in a fixture 53 in one embodiment of this invention is shown in FIG. 2. In this particular embodiment, the detector module 50 comprises the following components: a support structure 52, an electronic flex connector 54, two pins 55, two spacers 56, a diode 57, two scintillator packs 58, and a collimator assembly 59.

Figure 3:
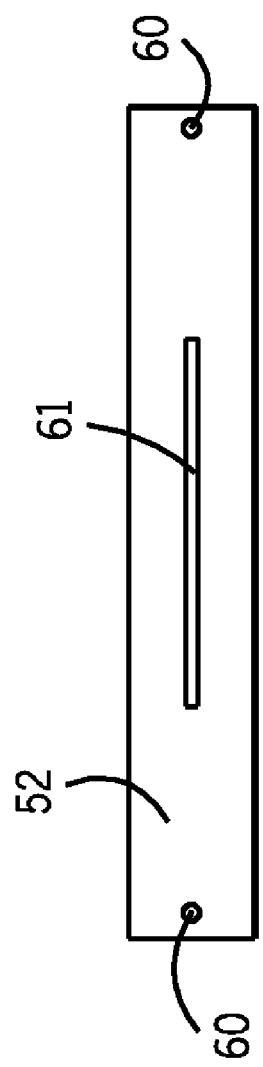
FIG. 3 is a top view of a support structure utilized in embodiments of this invention.
Figure 4:
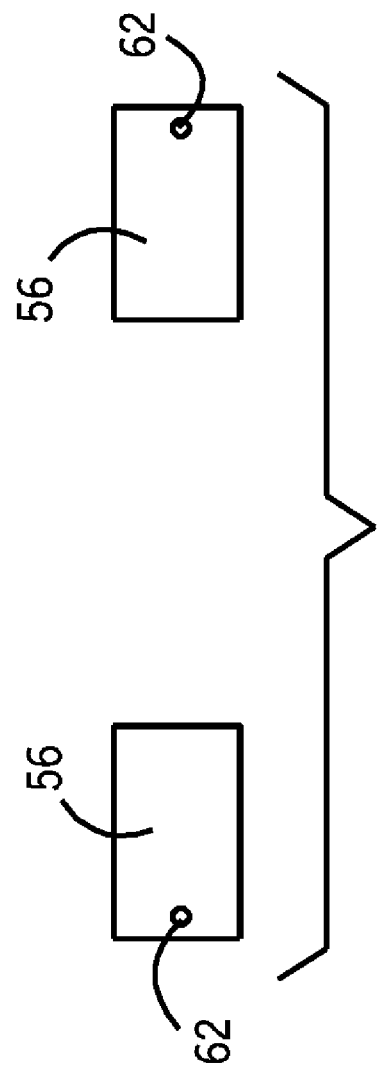
FIG. 4 is a top view of the spacers utilized in embodiments of this invention.

In embodiments, the support structure 52 for the detector modules 50 may be made of any suitable high stiffness material, such as for example, compression molded carbon fiber. As shown in FIG. 3, the support structure 52 preferably comprises a rectangular shaped piece of material having an elongated slot 61 in its central portion and apertures 60 proximate each end. The final support structure also comprises two spacers 56, as shown in FIG. 4. Each spacer 56 may be made of any suitable material, and preferably comprises an aperture 62 proximate one end where a pin 55 may be inserted. The pins 55 on the spacer/pin assemblies provide the reference points or reference frame 63 against which all other components of the detector module 50 will be aligned during assembly. As such, the top 70 and bottom 71 surfaces of each spacer 56 preferably have tight flatness and co-planarity requirements. Furthermore, the pins 55 preferably have tight diameter requirements and, when pressed into the spacers 56, have tight perpendicularity requirements with the top 70 and bottom 71 surfaces of the spacers 56.

Preferably, the detector modules 50 are assembled in an assembly fixture so that the detector components can be precisely and accurately assembled and attached to one another.

For example, the pins 55 may extend from the spacers 56 through the support structure 52 and into precisely located apertures in the assembly fixture.

In embodiments, support structure 52 may be inserted into the assembly fixture 53. Next, the pins 55 may be inserted into the apertures 62 in spacers 56, which may comprise press-fitting the pins 55 into slightly smaller apertures 62 in spacers 56. The spacer/pin assemblies may then be bonded or otherwise attached to support structure 52 in any suitable manner. Once the spacers 56, pins 55 and support structure 52 are assembled, the free end of the electronic flex connector 54, which preferably has its other end bonded or otherwise attached to the back surface of diode 57, may then be fed through the elongated slot 61 in support structure 52. Diode 57 is the active portion of the detector module 50. The free end of electronic flex connector 54 carries the electrical signals from the diode 57 to the read-out chips in a data acquisition system in a manner well know in the industry. The diode 57 (i.e., the back-bonded diode in this embodiment) may be aligned relative to the assembly fixture 53 and support structure 52 in any suitable manner, such as by optically or mechanically aligning features on the top of the diode 57 to the pins 55, and then the flex connector/diode assembly may be attached to the support structure 52 in any suitable manner. Scintillator packs 58 may then be aligned relative to the assembly fixture 53 and support structure 52 in any suitable manner, such as by optically or mechanically aligning features on the top of the scintillator packs 58 to the pins 55, and the scintillator packs 58 may then be optically coupled to the diode 57 in any suitable manner, such as by bonding or gluing. The scintillator packs 58 detect the x-rays, and then convert the x-rays into photons (i.e., visible light) that can be detected by the diode 57. Thereafter, in embodiments, a collimator assembly 59 that was specifically designed to align off pins 55 may be aligned with and operatively coupled to detector module 50 in any suitable manner, such as by placing precisely-located apertures in the collimator assembly over the pins 55. The collimator assembly 59 shapes the detected x-rays to the focal spots of the detectors so as to reduce the scattered radiation caused by off-focal alignment. Gaps 51 may be present between the spacers 56 and the active portion of the detector module 50 (i.e., the active portion of the detector module comprises the electronic flex connector 54, the diode 57 and the scintillator packs 58).

The completed detector module assembly 50 preferably has pins 55 protruding beyond the surface of the collimator assembly 59 so that the detector module 50 can be assembled directly into the CT imaging system 10, preferably via a precisely-located slot 21 on the support rail(s) 11 of the CT imaging system 10 into which pins 55 may be inserted. In this manner, there should be no need to adjust alignment of the detector module 50 with the support rails 11, since the diameter of each pin 55 is preferably only a few microns smaller than the slot(s) 21 on the support rails 11. While the other ends of pins 55 are shown extending beyond the surface of the support structure 52, this may or may not be necessary, depending on the particular CT imaging system the detector module 50 will be attached to.

As described above, the systems and methods of the present invention allow the detector elements in CT imaging systems to be accurately and more easily assembled than currently possible. Advantageously, the modular pin-based design of these support structures provides for the simple alignment of all relevant components (i.e., diode, scintillator packs, collimator, etc.) to the same pin(s), which is utilized as a local reference point for the entire detector module. Additionally, this design is easily and continuously extensible in the Z-direction, allowing additional rows of detector modules to be added to lengthen the coverage in the Z-direction. This invention allows each successive row of detector modules to be positioned close enough to one another so that gaps in Z-coverage are avoided. This is particularly advantageous since the medical industry now desires to have longer Z-coverage so that they can get more coverage of a patient with each rotation of the gantry, thereby allowing full organ imaging in a single CT scan.

Various embodiments of the invention have been described in fulfillment of the various needs that the invention meets. It should be recognized that these embodiments are merely illustrative of the principles of various embodiments of the present invention. Numerous modifications and adaptations thereof will be apparent to those skilled in the art without departing from the spirit and scope of the present invention. Thus, it is intended that the present invention cover all suitable modifications and variations as come within the scope of the appended claims and their equivalents.

What is claimed is:

1. A CT imaging system comprising:
   a detector module comprising:
   at least one back-bonded diode;
   a support structure having an elongated slot therein;
   a first and a second spacer;
   no more than two alignment pins including:
   a first alignment pin attached to the first spacer; and
   a second alignment pin attached to the second spacer;
   a plurality of detector components attached to the support structure and aligned relative to each of the first and second alignment pins; and
   a flex connector attached to a planar surface of the back-bonded diode and passing through the elongated slot of the support structure.

2. The CT imaging system of claim 1 wherein the plurality of detector components comprises, and at least one scintillator pack, and the at least one scintillator pack is attached to the at least one diode.

3. The CT imaging system of claim 2 wherein the at least one diode and the at least one scintillator pack are aligned with one of an optical and a mechanical alignment feature on the diode and on the at least one scintillator pack.

4. The CT imaging system of claim 2 further comprising a collimator assembly attached to the detector module, the collimator assembly having a first aperture and a second aperture, the collimator assembly aligned relative to the plurality of detector components via the first and second pins, wherein the first and second apertures in the collimator assembly are positioned thereon.

5. The CT imaging system of claim 2 wherein the at least one diode is a back-bonded diode.

6. The CT imaging system of claim 1 wherein the first and second pins are positioned in the first and second spacers, and the first and second pins are aligned perpendicular to a top surface and a bottom surface of the first and second spacers.

7. A CT imaging system comprising:
   a support rail;
   a detector module comprising:
   a support structure;
   a back-bonded diode;
   a first and a second spacer;
   no more than two alignment pins including:
   a first alignment pin attached to the first spacer; and
   a second alignment pin attached to the second spacer;
   a plurality of detector components attached to the support structure and aligned relative to each of the first and second alignment pins; and a flex connector positioned between the back-bonded diode and the support structure;
wherein the detector module is aligned to the support rail via the first pin and the second pin, wherein one of the first pin and the second pin are positioned within an alignment slot in the support rail.

8. A CT imaging system comprising:
a support rail;
a detector module comprising:
at least one back-bonded diode;
a support structure;
a first spacer having a first aperture, and a second spacer having a second aperture;
two alignment pins including:
a first alignment pin press-fit into the first aperture of the first spacer; and
a second alignment pin press-fit into the second aperture of the second spacer;
a plurality of detector components attached to the support structure and aligned relative to each of the first and second alignment pins; and
a flex connector attached to the back-bonded diode and positioned between the at least one back-bonded diode and the support structure;
wherein the detector module is aligned to the support rail via the first pin and the second pin, wherein one of the first pin and the second pin are positioned within an alignment slot in the support rail.

9. A method for assembling a CT detector, the method comprising:
forming a local reference frame with two alignment pins removably positioned in an assembly fixture, each centrally located along a width of the CT detector;
attaching a flex connector to a surface of at least one diode;
aligning a support structure, at least two spacers, and the two centrally located alignment pins to one another;
passing the flex connector through a slot of the support structure;
operatively coupling the support structure, the at least two spacers, and the two centrally located alignment pins to one another to form a support structure sub-assembly;
aligning a the at least one diode relative to the local reference frame; and
operatively coupling the plurality of detector components to the support structure sub-assembly to form the CT detector.

10. The method of claim 9 further comprising extending the two centrally located alignment pins from the spacers, through the support structure, and into apertures in the assembly fixture.

11. The method of claim 9 wherein the plurality of detector components comprises an electronic flex connector, at least one diode, and at least one scintillator pack, and further comprising operatively coupling the electronic flex connector to the at least one diode, and operatively coupling the at least one scintillator pack to the at least one diode.

12. The method of claim 11 further comprising precisely aligning the electronic flex connector, the at least one diode, and the at least one scintillator pack to the two centrally located alignment pins.

13. The method of claim 9 further comprising aligning a collimator assembly to the plurality of detector components via the two centrally located alignment pins and operatively coupling it thereto.

14. The method of claim 9 further comprising aligning the plurality of detector components relative to a CT imaging system via the two centrally located alignment pins and operatively coupling it thereto.

15. The method of claim 9 wherein upon inserting the two centrally located alignment pins into the at least two spacers, the two centrally located alignment pins meet a predetermined perpendicularity requirement with a top surface of the spacer and a bottom surface of the spacer.

16. A system for assembling a precisely-aligned detector module, the system comprising:
a means for aligning a support structure, at least two spacers, and at least two alignment pins to one another;
a means for operatively coupling the support structure, the at least two spacers, and the at least two alignment pins to one another to form a support structure sub-assembly;
a means for aligning a detector component relative to the at least two alignment pins; and
a means for operatively coupling the detector component to the support structure sub-assembly,
wherein the at least two alignment pins are utilized as local reference points against which the support structure, the at least two spacers, and the detector component are precisely aligned;
wherein the support structure has an elongated slot therein; and
wherein the at least two alignment pins are positioned in the at least two spacers, and the at least two alignment pins are aligned perpendicular to a top surface and a bottom surface of the spacers.

17. The system of claim 16 wherein an assembly fixture is utilized to align and assemble the detector module.

18. The system of claim 16 wherein the detector component comprises an electronic flex connector, at least one diode, and at least one scintillator pack, wherein the electronic flex connector is operatively coupled to the at least one diode, and the at least one scintillator pack is operatively coupled to the at least one diode.

19. The system of claim 18 wherein the electronic flex connector, the at least one diode, and the at least one scintillator pack are aligned relative to the at least two alignment pins.

20. The system of claim 16 further comprising a means for aligning and operatively coupling a collimator assembly to the precisely aligned detector module via the at least two alignment pins.

21. The system of claim 16 further comprising a means for operatively coupling the detector module to a CT imaging system via the at least two alignment pins.

* * * * *